(12) United States Patent
Han et al.

(10) Patent No.: US 6,997,185 B2
(45) Date of Patent: Feb. 14, 2006

(54) ADJUSTABLE AUXILIARY APPARATUS OF STABLE AIR CONDITIONING FOR HUMAN RESPIRATORY SYSTEM

(75) Inventors: Tai-Kang Han, 2F, No. 12, Lane 366, Ta-Ming Rd., Tali City, Taichung Hsien (TW); Hua Ting, 4F, No. 165, Sec. 1, Chienkuo S. Rd., Taichung (TW)

(73) Assignees: Tai-Kang Han, Tali (TW); Hua Ting, Taichung (TW)

( * ) Notice: Subject to any disclaimer, the term of this patent is extended or adjusted under 35 U.S.C. 154(b) by 204 days.

(21) Appl. No.: 10/736,510

(22) Filed: Dec. 17, 2003

(65) Prior Publication Data

US 2005/0133031 A1 Jun. 23, 2005

(51) Int. Cl.
*A61M 16/00* (2006.01)
*A62B 7/00* (2006.01)

(52) U.S. Cl. .......................... 128/204.17; 128/204.18; 128/203.16; 261/130

(58) Field of Classification Search ........... 128/204.17, 128/204.18, 204.21, 204.23, 204.25, 203.16–203.17, 128/203.26, 203.27, 205.27, 205.29, 201.13; 261/104, 107, 130, 154, DIG. 65
See application file for complete search history.

(56) References Cited

U.S. PATENT DOCUMENTS

| | | | | |
|---|---|---|---|---|
| 2,130,327 A | * | 9/1938 | Galson | 62/262 |
| 4,080,103 A | * | 3/1978 | Bird | 417/3 |
| 4,475,358 A | * | 10/1984 | Seifert et al. | 62/186 |
| 4,794,922 A | * | 1/1989 | DeVries | 128/204.18 |
| 5,673,687 A | * | 10/1997 | Dobson et al. | 128/204.14 |

* cited by examiner

*Primary Examiner*—Henry Bennett
*Assistant Examiner*—Shumaya B. Ali
(74) *Attorney, Agent, or Firm*—Genus Law Group LLP

(57) ABSTRACT

An adjustable air conditioning and regulation apparatus for human respiratory system includes an air treatment assembly and a host controlling assembly. The air treatment assembly has an air filter, a humidity control, a heating device for temperature control and a pressure control. The air filter removes the particles and smells from the air. The clean air is regulated by the controls that maintain the clean air at a desired level of temperature, pressure and humidity. The apparatus provides clean, fresh and comfortable air for the patients with compromised respiratory system.

12 Claims, 7 Drawing Sheets

ADJUSTABLE AUXILIARY APPARATUS OF STABLE AIR CONDITIONING FOR HUMAN RESPIRATORY SYSTEM

BACKGROUND OF THE INVENTION

1. Field of the Invention

The present invention relates to a medical appliance related field, and more particularly to an air conditioning and regulation apparatus that provide purified air at proper levels of temperature, pressure and humidity for a person whose respiratory system may be defective.

2. Description of Related Art

The ambient air that we breathe everyday contains many contaminants, such as toxic particles, bacterium and allergenic substances. A person who has chronic pulmonary diseases particularly needs clean and fresh air to breathe. In addition to the requirements of purified air, adequate levels of air temperature and humidity must be controlled to maintain the air conditions in an optimized state to meet demands of air exchanging in alveoli, especially in a compromised respiratory system of the pulmonary diseased person. Conventional air conditioners do not have a combined function of cleaning the air and regulating simultaneously certain levels of the air and are thus not able to provide a suitable atmospheric condition for people in general and those suffering pulmonary diseases, such as upper or lower airway related diseases in particular.

Therefore, the present invention provides an air conditioning and regulation apparatus for pulmonary diseased persons to address the aforementioned problems so as to reduce stress of the respiratory system of a diseased person and avoid a further injure in respiratory passage, such as trachea and bronchus.

SUMMARY OF THE INVENTION

The main objective of the invention is to provide an improved air conditioning and regulation apparatus that removes contaminating particles and odors from the air and regulates the clean air to desired levels of temperature, pressure and humidity.

The present invention mainly comprises an air treatment assembly and a host controlling assembly. The air treatment assembly comprises an air filter, a humidity control and a heating device for temperature control. The air filter removes the particles and smells from the air. The clean air is regulated and conditioned by the three aforesaid controls that hold the clean air to desired levels of temperature, pressure and humidity.

The host controlling assembly controls and actuates the air treatment assembly to achieve the aforesaid goal that is to provide clean, fresh and comfortable air for the pulmonary diseased person to breathe.

Other objectives, advantages and novel features of the invention will become more apparent from the following detailed description when taken in conjunction with the accompanying drawings.

DETAILED DESCRIPTION OF PREFERRED EMBODIMENT

Figure 1:
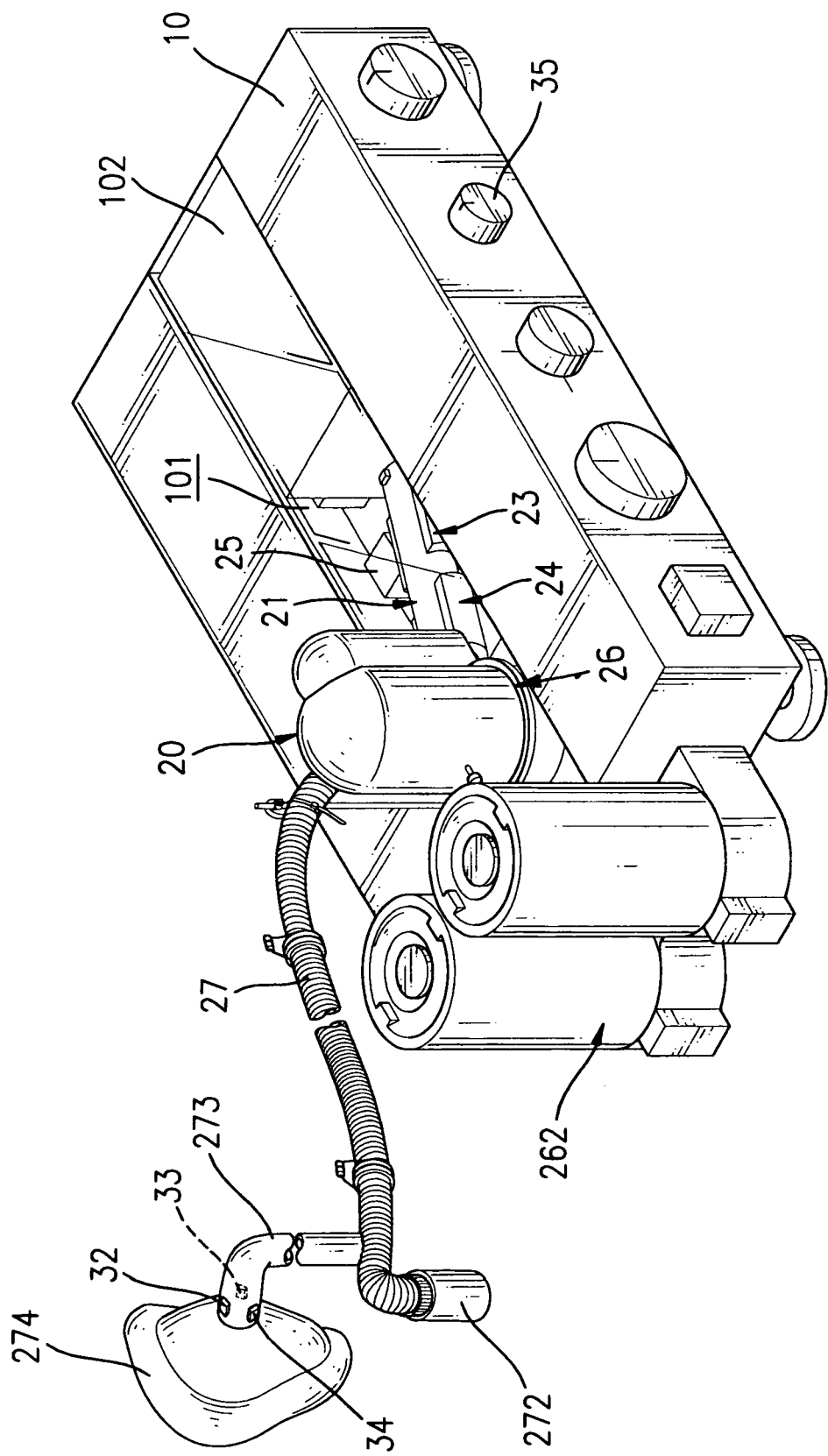
FIG. 1 is an enlarged perspective view of a preferred embodiment in accordance with the present invention.

With reference to FIGS. 1 to 4 and 7, a preferred embodiment of the present invention comprises a platform (10), an air treatment assembly (20), a host controlling assembly (30) and a display (40). The air treatment assembly (20) is mounted in the platform (10) to treat and clean air. The host controlling assembly (30) controls and actuates the air treatment assembly (20) to maintain adequate levels of air temperature and humidity of clean air. The platform (10) has a front (not numbered), a rear (not numbered), a top (not numbered), a bottom (not numbered), a left side (not numbered), a right side (not numbered), a channel (101) and a filter case (102). The channel (101) is defined transversally in the top and is elongated from the left side to the right side. The filter case (102) is mounted in the platform (10) at the right side and protrudes partially into the channel (101). The filter case (102) has an intake air entrance (103) and an air exit (104) that are formed opposite to each other.

Figure 4:
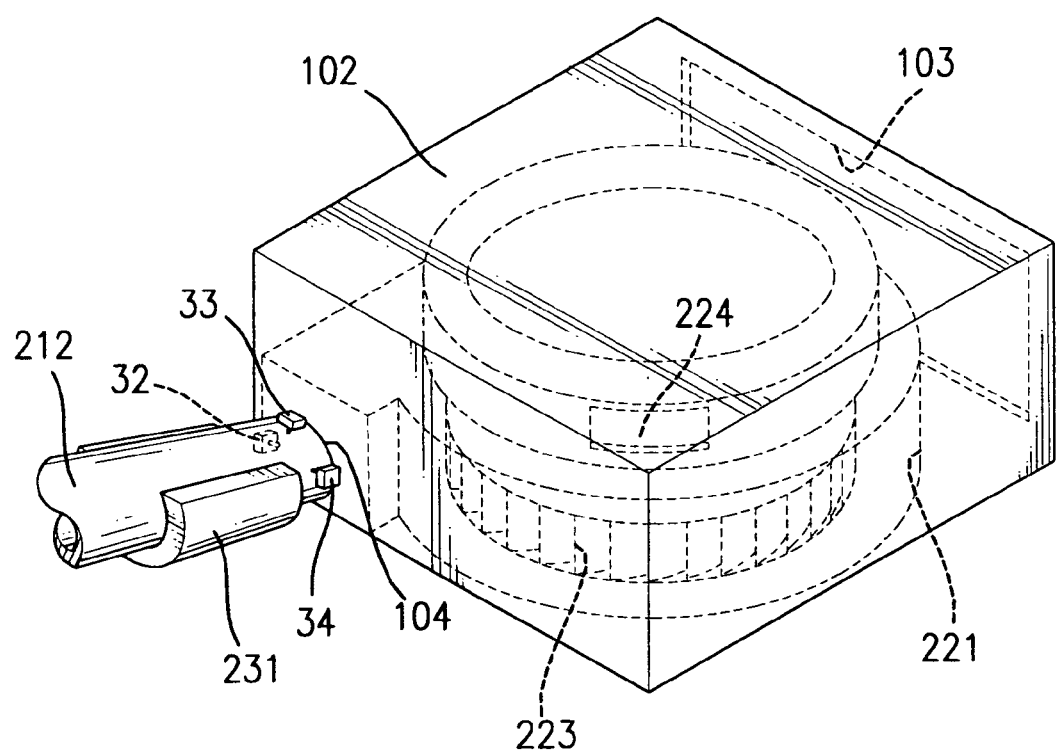
FIG. 4 is an enlarged perspective view of an air filter in a filter case of the preferred embodiment in FIG. 1.
Figure 5:
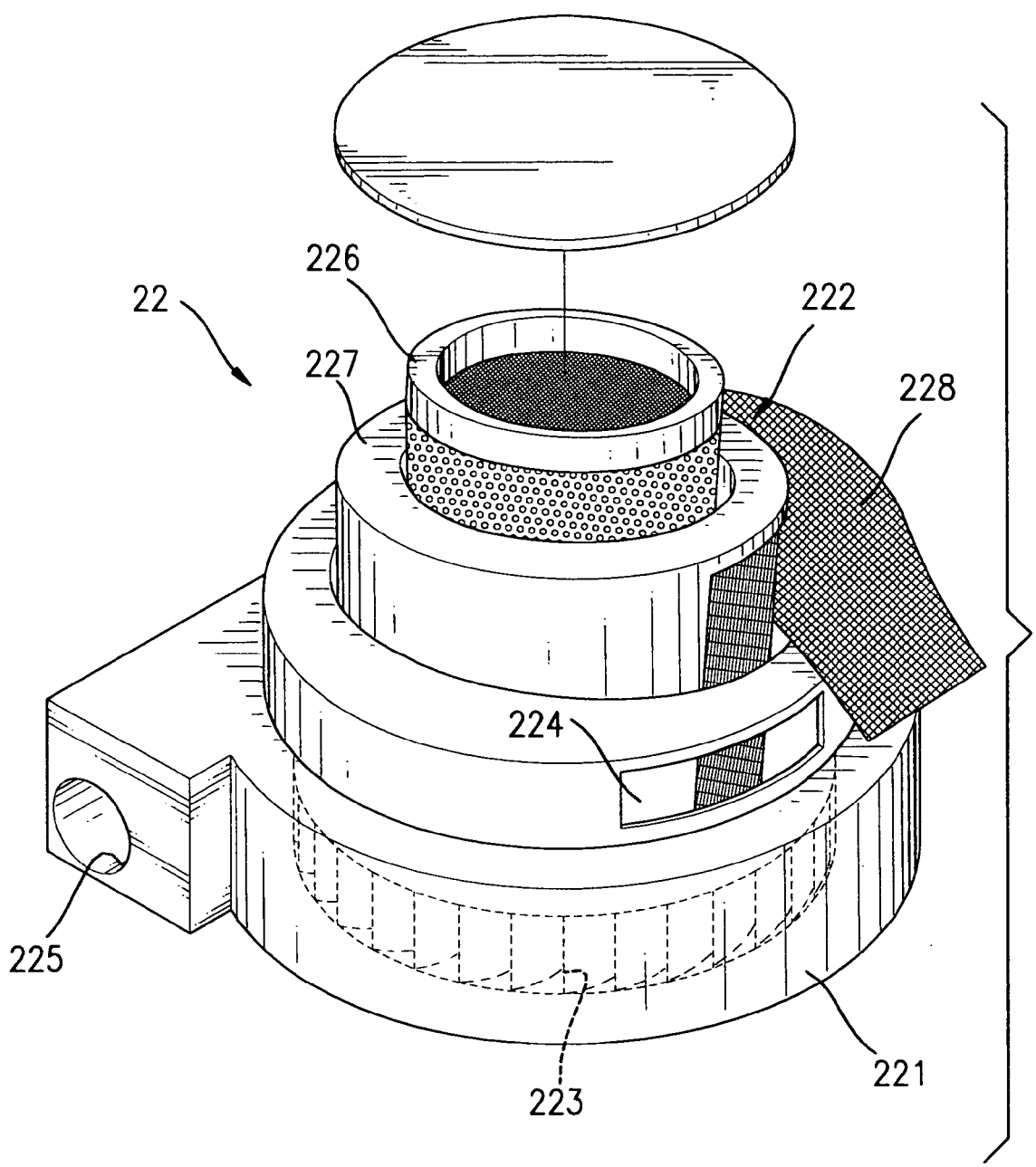
FIG. 5 is an enlarged, exploded perspective view of the air filter in FIG. 4.

The air treatment assembly (20) is mounted in the platform (10) to condition and regulate the incoming air and comprises an air duct (21), an air filter (22), a humidity control (23), a heating device (24), an optional ozone generator (25), a water vapor generator (26) and a clean air venting hose (27). With further reference to FIGS. 4 and 5, the air filter (22) is mounted in the filter case (102) and comprises a housing (221), a filtering core (222) and a powered fan (223). The housing (221) is mounted in the filter case (102) and has an air inlet (224) and an air outlet (225). The air outlet (225) is aligned with the air exit (104) of the filter case (102). The filtering core (222) is mounted in the housing (221) to remove the particle contaminants from the incoming air. The powered fan (223) is driven by a motor (not shown) and is mounted in the filtering core (222) to draw the air that passes through the intake air entrance (103) of the filter case (102) to pass through the filtering core (222). The filtering core (222) removes the contaminants, such as particles, odorous substances and the like from the air.

The filtering core (222) of the air filter (22) may comprise an inside filtering cage (226), an outside filtering cage (227) and a filtering fine mesh (228). The inside filtering cage (226) is porous, is mounted inside the outside filtering cage (227) and has a smell adsorption mixture of active carbon, potassium permanganate, zeolite etc to adsorb odors from the incoming air. The outside filtering cage (227) is also porous and is made of a fabric of irregular fiberglass and fiber to remove the particles that are less than a diameter of 0.3 microns. The filtering fine mesh (228) wraps radially around the outside filtering cage (227), contains active carbon and is used to remove the particles that are larger than a diameter of 0.3 microns.

Figure 2:
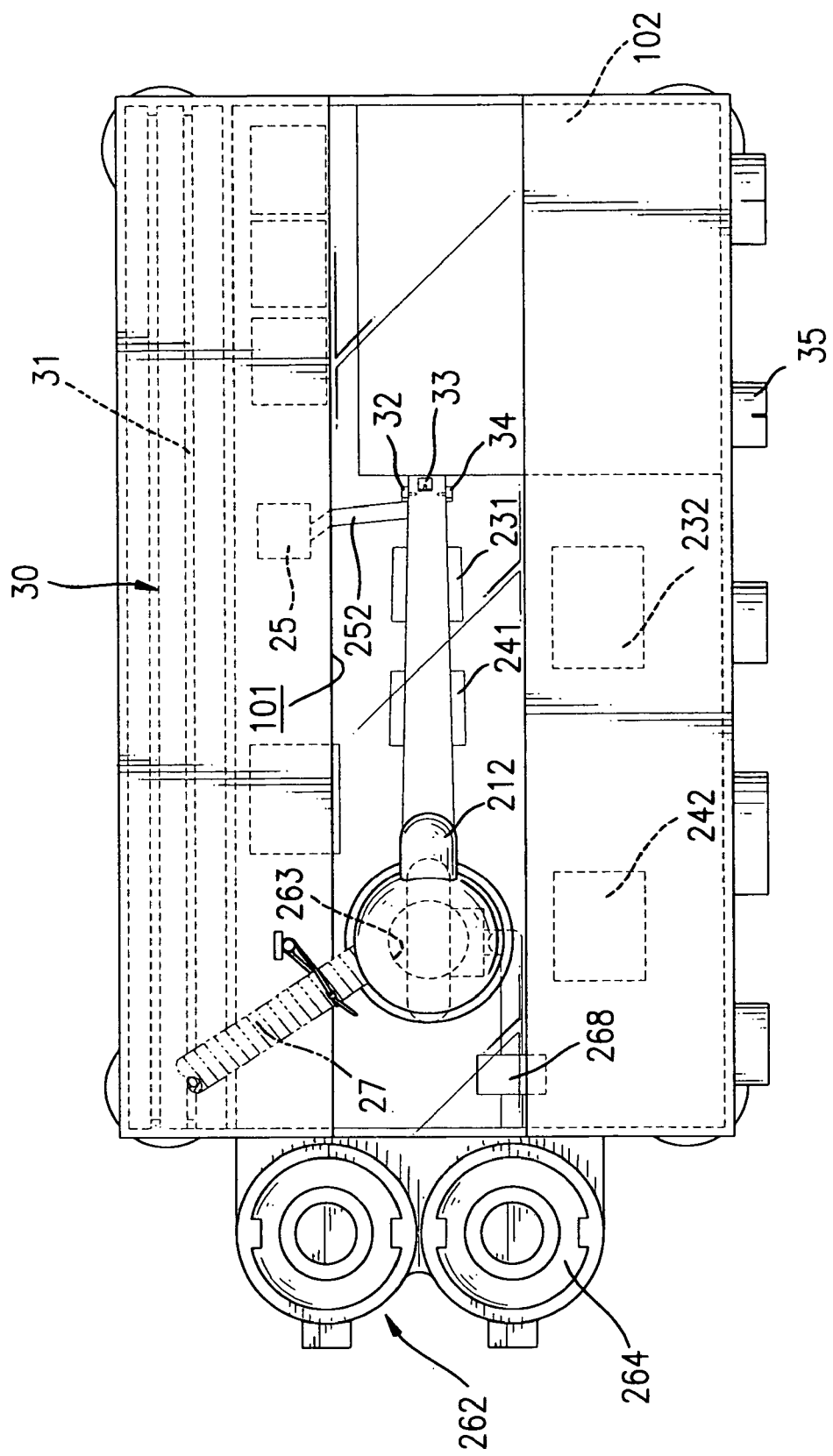
FIG. 2 is an enlarged top plan view of the preferred embodiment in FIG. 1.
Figure 3:
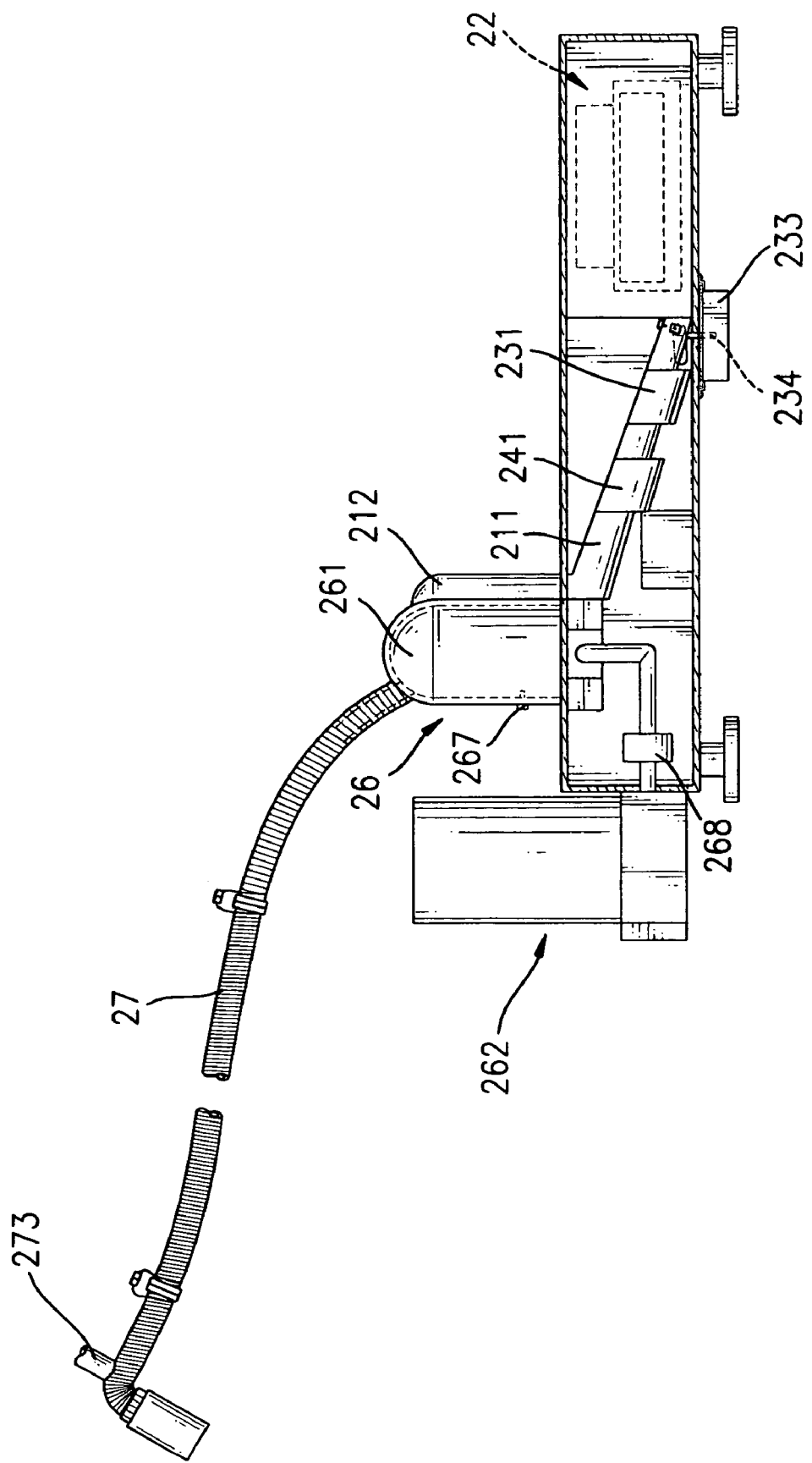
FIG. 3 is an enlarged side elevation plan view of the preferred embodiment in FIG. 1.

With reference to FIGS. 2, 3 and 5, the air duct (21) is transparent, is mounted in the channel (101) and has a transverse segment (211), a vertical segment (212) an interior periphery (not numbered), an exterior periphery (not numbered), a narrowed end (not numbered) and a top end (not numbered). The transverse segment (211) is tapered. The narrowed end is formed at the transverse segment (211) and is fitted and held in the aligned air exit (104) and air outlet (225). The top end is formed in the vertical segment (212). The interior periphery of the air duct (21) is provided with a layer of thin film of photo catalysis, such as titanium dioxide ($TiO_2$). Therefore, the bacterium or virus will be killed by the photo catalysis as the air passes through the air duct (21) as light transmits through the air duct (21).

The humidity control (23) is mounted in the platform (10) and comprises a condenser (231), a condenser controller (232), a drain pan (233) and a drain hose (234). The condenser (231) is mounted on the exterior periphery of the transverse segment (211) and is controlled by the condenser controller (232). The drain pan (223) is mounted on the bottom of the platform (10) to collect condensed water. The drain hose (234) is attached to the exterior periphery of the transverse segment (211) at a position below the condenser (231) and has two open ends (not numbered). The ends respectively extend into the transverse segment (211) and the drain pan (233) to permit the condensed water to enter the drain pan (233).

The heating device (24) is mounted in the platform (10) and comprises a heater (241) and a heater controller (242). The heater (241) is mounted on the exterior periphery of the transverse segment (211) at a position over the condenser (231) and is controlled by the heater controller (242) to heat the air that passes through the air duct (21).

The ozone generator (25) is mounted in the platform (10) and has a connecting hose (252). The connecting hose (252) connects to the transverse segment (211) so that ozone generated by the ozone generator (25) can enter the transverse segment (211) through the connecting hose (252) to disinfect the filtered air that comes out of the air filter (22).

The water vapor generator (26) is mounted on the platform (10), connects to the air duct (21) and comprises a water vapor tank (261), a supplementary water device (262), an ultrasonic generator (263) and a water level controlling device (not numbered). The water vapor tank (261) has a top (not numbered), a bottom (not numbered) and an inner space (not numbered). The top end in the vertical segment (212) of the air duct (21) connects to the water vapor tank (261) at the top of the water vapor tank (261). The water vapor tank (261) contains the water in the inner space. The supplementary water device can be two or more supplementary water tanks (264) and is attached to the left side of the platform (10). The two supplementary water tanks (264) communicate with the water vapor tank (261) at the bottom by means of a pipe (not numbered). The water level controlling device comprises a water level switch (267) and a flow control valve, such as an electromagnetic valve (268). The water level switch (267) is attached to the water vapor tank (261) at a high of 5 to 8 centimeters and electrically connects to the electromagnetic valve (268). The electromagnetic valve (268) controls the flow of water in the pipe to allow the water in the supplementary water tanks (264) enter the water vapor tank (261) as the water level switch (267) is triggered so as to keep the water in the water vapor tank (261) at the given height. The ultrasonic generator (263) is mounted at the bottom of the water vapor tank (261) to produce ultrasonic waves to vibrate the water molecules in the water vapor tank (261) so that a small amount of the water becomes water vapor filling the inner space. The moist inner space is used to increase a degree of humidity in the air that passes through the water vapor tank (261).

Figure 6:
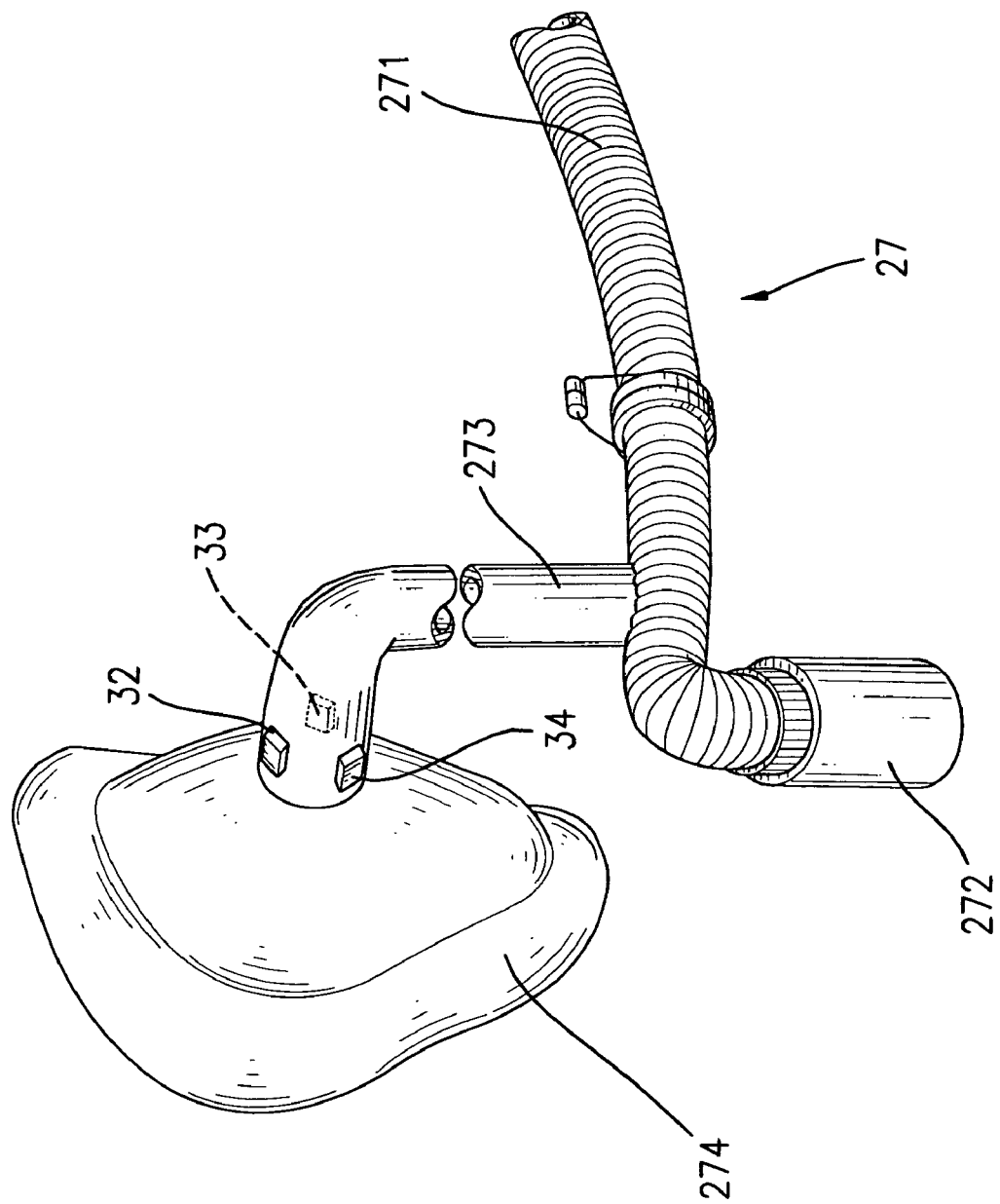
FIG. 6 is an exploded perspective view of a segment of a clean air venting hose of the preferred embodiment.
Figure 7:
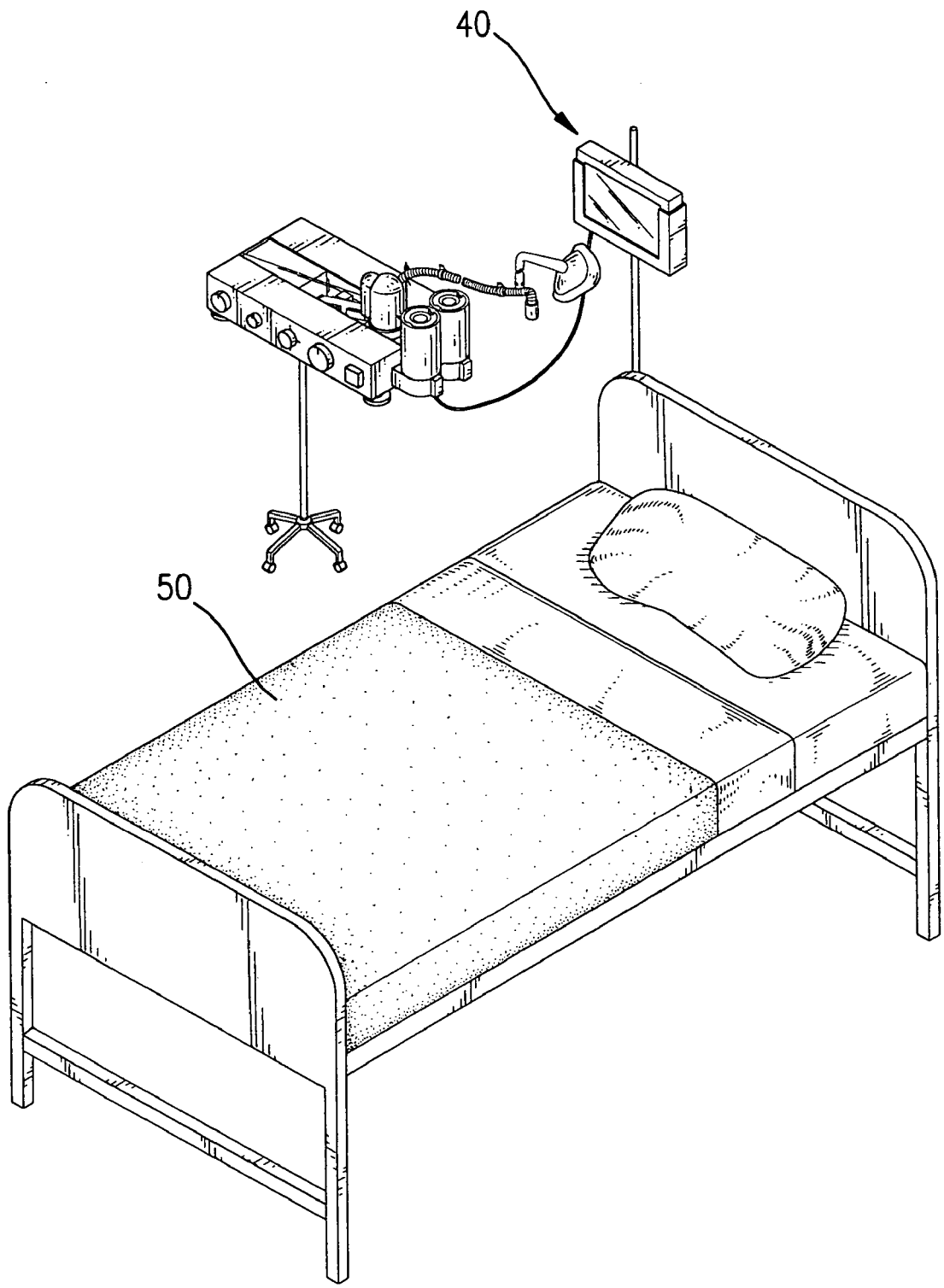
FIG. 7 is an operational perspective view of the preferred embodiment in FIG. 1, when the preferred embodiment of the present invention is used beside a sickbed.

With further reference to FIG. 6, the clean air venting hose (27) is flexible and connects to the water vapor tank (261) at the top of the water vapor tank (261). The clean air venting hose (27) can be assembled of multiple separated segments (271) and has a proximal end (not numbered), a distal end (not numbered), a connector (272), a connecting duct (273) and a thermostat heating coil (not numbered). The proximal end connects to the water vapor tank (261) at the top. The connector (272) and the connecting duct (273) are respectively formed at the distal end. The thermostat heating coil wraps around the clean air venting hose (27) to hold the air temperature at a given level. The connecting duct (273) is used to connect the air venting hose (27) to a facemask (274), a tracheal cannula (not shown) or the like for providing the clean air to the person who has the pulmonary disease.

The host controlling assembly (30) comprises a modular controlling circuit board (31), multiple control knobs (35) and multiple sensing elements, such as pressure sensors (32), humidity sensors (33) and temperature sensors (34). The sensors (32, 33, 34) are respectively mounted on the transverse segment (211) near the narrowed end and either the end of the connecting duct (274) or the clean air venting hose (27) near the distal end. The modular controlling circuit board (31) operates a servo control system and electrically connects to the ozone generator (25), the controllers (232, 242), the ultrasonic generator (263) of the water vapor generator (26), the powered fan (223) and the control knobs (35). Consequently, the modular controlling circuit board (31) can control and actuate the condenser (231), the heater (241), the ozone generator (25) and the water vapor generator (26) with an adequate timing.

The display (40), such as a liquid crystal display (LCD) monitor may be mounted on the top of the platform (10), a separated tripod stand (not shown) or on a bed (50) and electrically connects to the modular circuit board (31). The display (40) can indicate the conditions of the air for care givers or users themselves. A desired degree of temperature, pressure and humidity in the air can be set by means of the control knobs (35) and start the fan (223). The air filter (22) removes the contaminants and smells from the incoming air. The purified air enters the air duct (21), and the sensors (32, 33, 34) detect the current pressure, temperature and humidity in the purified air. If the humidity degree is higher than the set value, then the humidity control (23) works to condense the moist air. The condensed water will be collected in the drain pan (233). If the humidity degree is lower than the set value, then the water vapor generator (26) works to produce water vapor to moisten the purified air. Likewise, if the air temperature is less than the set value, then the heating device (24) works to heat the air. If the air temperature is higher than the set value, the humidity control (23) works to cool the purified air. If the pressure of the air in the air duct (21) is higher than the set value, then the revolution speed of the fan (223) is reduced. If the pressure of the air in the air duct (21) is lower than the set value, then the revolution speed of the fan (223) is increased.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the scope of the appended claims.

What is claimed is:

1. An adjustable auxiliary apparatus of stable air conditioning for human respiratory system and the apparatus comprising:
   a platform having a top, a bottom, a channel defined transversally in the top and a filter case having an intake air entrance and an air exit;
   an air treatment assembly mounted in the platform and comprising
      an air filter mounted in the filter case and comprising
         a housing mounted in the filter case and having an air inlet communicating with the intake air entrance and an air outlet aligned with the air exit;
         a filtering core mounted in the housing; and
         a powered fan mounted in the filtering core to draw air inward the housing;
      an air duct mounted in the channel and having a transverse segment, a vertical segment, an interior periphery, an exterior periphery, a narrowed end and a top end, the narrowed end formed at the transverse segment and being fitted and held in the aligned air exit and air outlet, and the top end formed at the vertical segment;
      a humidity control mounted in the platform and comprising a condenser mounted on the exterior periphery of the air duct on the transverse segment and a condenser controller to control the condenser;
      a heating device mounted in the platform and comprising a heater mounted on the exterior periphery of the air duct on the transverse segment and a heater controller to control the heater;
      a water vapor generator mounted on the platform and comprising
         a water vapor tank with a top, a bottom and an inner space connected to the vertical segment of the air duct where the top end in the vertical segment of the air duct connects to the water vapor tank at the top; and
         an ultrasonic generator mounted at the bottom of the water vapor tank to produce ultrasonic waves; and
      a clean air venting hose connected to the water vapor tank at the top of the water vapor tank; and
   a host controlling assembly mounted in the platform and comprising
      a modular controlling circuit board operating a servo control system and connected electrically to the condenser and heater controllers, the powered fan of the air filter and the ultrasonic generator of the water vapor generator;
      multiple control knobs connected electrically to the modular controlling circuit board; and
      multiple sensing elements mounted respectively on the transverse segment at the narrowed end and the clean air venting hose.

2. The apparatus as claimed in claim 1, wherein the filtering core of the air filter comprises
   a porous outside filtering cage made of a fabric of irregular fiberglass and fiber;
   a porous inside filtering cage mounted in the outside filtering cage and having a smell adsorption mixture of active carbon, potassium permanganate and zeolite; and
   a filtering fine mesh contains active carbon wrapped radially around the outside filtering cage.

3. The apparatus as claimed in claim 1, wherein water vapor generator further comprises
   a supplementary water device having at least one supplementary water tank communicating with the water vapor tank at the bottom; and
   a water level controlling device comprising
      an electromagnetic valve to control flow of water out of the at least one supplementary water tank to enter the water vapor tank; and
      a water level switch attached to the water vapor tank and electrically connected to the electromagnetic valve.

4. The apparatus as claimed in claim 1, wherein the air treatment assembly further comprises an ozone generator mounted in the platform, controlled by the modular controlling circuit board and having a connecting hose connected to the transverse segment to generate ozone to enter the transverse segment.

5. The apparatus as claimed in claim 1, wherein the interior periphery of the air duct has a layer of thin film of photo catalysis, titanium dioxide ($TiO_2$).

6. The apparatus as claimed in claim 1, wherein the clean air venting hose has multiple separated segments, a connector, a connecting duct and a thermostat heating coil wrapped around the clean air venting hose to maintain the air temperature in the clean air venting hose at a given level.

7. The apparatus as claimed in claim 1 further comprising a separated display electrically connected to the modular circuit board to show air conditions handled by the apparatus.

8. The apparatus as claimed in claim 2, wherein the water vapor generator further comprises
   a supplementary water device having at least one supplementary water tank communicating with the water vapor tank at the bottom; and
   a water level controlling device comprising
      an electromagnetic valve to control flow of water out of the at least one supplementary water tank to enter the water vapor tank; and
      a water level switch attached to the water vapor tank and electrically connected to the electromagnetic valve.

9. The apparatus as claimed in claim 8, wherein the air treatment assembly further comprises an ozone generator mounted in the platform, controlled by the modular controlling circuit board and having a connecting hose connected to the transverse segment to generate ozone to enter the transverse segment.

10. The apparatus as claimed in claim 9, wherein the interior periphery of the air duct has a layer of thin film of photo catalysis, titanium dioxide ($TiO_2$).

11. The apparatus as claimed in claim 10, wherein the clean air venting hose has multiple separated segments, a connector, a connecting duct and a thermostat heating coil wrapped around the clean air venting hose to maintain the air temperature in the clean air venting hose at a given level.

12. The apparatus as claimed in claim 11 further comprising a separated display electrically connected to the modular circuit board to show air conditions handled by the apparatus.

* * * * *